United States Patent
Koppelman et al.

(10) Patent No.: US 9,526,781 B2
(45) Date of Patent: Dec. 27, 2016

(54) PHARMACEUTICAL FORMULATIONS AND THE USE THEREOF FOR THE TREATMENT OF PEANUT ALLERGY

(71) Applicant: HAL Allergy Holding B.V., Leiden (NL)

(72) Inventors: Stefan Johan Koppelman, De Bilt (NL); Joanna Paulina Maria van der Kleij, Haarlem (NL)

(73) Assignee: HAL Allergy Holding B.V., Leiden (NL)

( * ) Notice: Subject to any disclaimer, the term of this patent is extended or adjusted under 35 U.S.C. 154(b) by 31 days.

(21) Appl. No.: 14/362,588

(22) PCT Filed: Dec. 14, 2012

(86) PCT No.: PCT/EP2012/075535
§ 371 (c)(1),
(2) Date: Jun. 3, 2014

(87) PCT Pub. No.: WO2013/087837
PCT Pub. Date: Jun. 20, 2013

(65) Prior Publication Data
US 2014/0363470 A1    Dec. 11, 2014

(30) Foreign Application Priority Data
Dec. 16, 2011 (WO) .................. PCT/EP2011/073037

(51) Int. Cl.
| | |
|---|---|
| *A61K 39/00* | (2006.01) |
| *A61K 39/35* | (2006.01) |
| *A61K 39/36* | (2006.01) |
| *A61K 39/38* | (2006.01) |
| *A61K 36/48* | (2006.01) |
| *A61K 33/06* | (2006.01) |

(52) U.S. Cl.
CPC .............. *A61K 39/35* (2013.01); *A61K 33/06* (2013.01); *A61K 36/48* (2013.01); *A61K 2039/577* (2013.01); *A61K 2236/331* (2013.01)

(58) Field of Classification Search
None
See application file for complete search history.

(56) References Cited

U.S. PATENT DOCUMENTS

2010/0086568 A1* 4/2010 Koppelman et al. ...... 424/275.1

FOREIGN PATENT DOCUMENTS

| WO | 2005/060994 A1 | 7/2005 |
| WO | 2010/000873 A1 | 1/2010 |

OTHER PUBLICATIONS

Van Der Kleij et al. "A Peanut Allergoid with Increased Safety and Maintained Immunogenicity", Journal of Allergy and Clinical Immunology, vol. 127, No. 2, Suppl. S, Feb. 2011, p. AB32.
Mattison et al. "Molecular Characterization of Ara h 1 Before and After Thermal Processing", Journal of Allergy and Clinical Immunology, vol. 127, No. 2, Suppl. S, Feb. 2011, p. AB113.
Nelson et al. "Treatment of anaphylactic sensitivity to peanuts by immunotherapy with injections of aqueous peanut extract", Journal of Allergy and Clinical Immunology, Mosby, Inc., US, vol. 99, No. 6, Jun. 1, 1997, pp. 744-751.
Koppelman et al. "Purification and immunoglobulin E-binding properties of peanut allergen Ara h 6: evidence for cross-reactivity with Ara h 2", Clinical & Experimental Allergy, vol. 35, No. 4, 1 Apr. 2005, pp. 490-497.

* cited by examiner

*Primary Examiner* — Nora Rooney
(74) *Attorney, Agent, or Firm* — Bret E. Field; Bozicevic, Field & Francis LLP (57) ABSTRACT

The present invention relates to compositions which can be used in immunotherapy and especially to compositions which can be used in immunotherapy for mammals, such as human mammals, suffering from peanut allergy. The present invention further relates to the use of the present compositions for the therapeutic treatment for desentizing the immune system of a mammal suffering from an allergy by immunotherapy and the use of the present compositions in a prophylactic treatment of a mammal with high predisposition to develop a certain allergy. Specifically, the present invention relates to pharmaceutical compositions comprising a modified whole peanut extract and pharmaceutically acceptable diluents and/or excipients, wherein said modified whole peanut extract is a reduced and subsequently alkylated whole peanut extract, preferably a whole defatted peanut extract comprising soluble peanut kernel proteins such as Ara h1, Ara h2 and Ara h6.

13 Claims, 9 Drawing Sheets

PHARMACEUTICAL FORMULATIONS AND THE USE THEREOF FOR THE TREATMENT OF PEANUT ALLERGY

The present invention relates to pharmaceutical formulations, or compositions, which can be used in immunotherapy and especially to formulations or compositions which can be used in immunotherapy for mammals, such as human mammals, suffering from peanut allergy. The present invention further relates to the use of the present formulations or compositions for the therapeutic treatment for desentizing the immune system of a mammal suffering from an allergy by immunotherapy and the use of the present formulations or compositions in a prophylactic treatment of a mammal with high predisposition to develop a certain allergy.

Allergen immunotherapy, also termed hyposensitization therapy, immunologic desensitization, hyposensibilization, or allergen-specific immunotherapy, is a form of immunotherapy for allergic disorders in which the patient is vaccinated with increasingly larger doses of an allergen, i.e. the substance, or substances, to which they are allergic, with the aim of inducing immunologic tolerance.

Allergen specific immunotherapy is the only treatment strategy which treats the underlying cause of an allergic disorder. It is a highly cost-effective treatment strategy and results in an improved quality of life.

Immunotherapy has been shown to produce long-term remission of allergic symptoms, to reduce severity of associated allergic response, as well to reduce the chances of new sensitizations to allergens developing. Immunotherapy aims to modulate the immune system's response to allergens.

Immunotherapy generally encompasses repeated exposure to a specific allergen via, for example, sublingual or subcutaneous routes, thereby providing a desensitization of the allergic patient to the allergen and thus a reduction in allergic symptoms and use of symptomatic based treatments.

The exact mechanism underlying immunotherapy is not fully known but it is accepted that immunotherapy leads to alteration of the immune response to an allergen. The modification at least comprises a change in IgE synthesis and the production of IgE blocking antibodies reducing the allergic response of the immune system to specific allergens. Also an increase in conversion of Th2 to Th1/T regulatory cells is observed. At a molecular level, part of the underlying mechanism relies on the preferential induction of allergen-specific IgG to neutralize an allergen and a reduction of allergen-specific IgE.

Immunotherapy generally involves exposing an allergic patient to low doses of an allergen. The dose is gradually increased on a regular, for example weekly, basis, until a "maintenance" dose is reached. This translates in approximately four months of weekly injections to reach the maintenance dose. Once the maintenance dose is reached, the injections are administered less often, for example once per month for a few years. Generally, the longer the treatment and the higher the dose, the greater the therapeutic benefit.

After successful completion of immunotherapy, long-term protection can be expected for a period of 3 to 5 years or more. Therapy can be repeated should symptoms begin to return or if the individual becomes exposed to new allergens that were not included in the previous treatment regimen.

Peanuts are one of the most common foods responsible for food-induced allergy. A curative treatment for peanut allergy is not yet available. Specific immunotherapy (SIT) using aqueous peanut extract displayed an increased tolerance to oral ingestion of peanuts. However, as reported by Nelson et al. (J. Allergy Clin. Immunol. 1997 June; 99(6 Pt 1):744-51), aqueous peanut extracts resulted in unacceptable systemic reactions, even during the maintenance injections. Accordingly, Nelson et al. concluded: "For clinical application of this method of treatment, a modified peanut extract is needed."

Major allergens in peanut allergy are the peanut seed storage proteins Ara h1 (vicilin) and Ara h2 (conglutin). In a recent study (Movérare et al., Int Arch Allergy Immunol; 2011; pp 282-290) most young adults with suspected peanut allergy had IgE antibodies to Ara h1 and Ara h2. Besides these major allergens also IgE reactivity against other peanut kernel proteins has been reported, for example Ara h6.

Modification of peanut allergens Ara h2 and Ara h6 by means of reduction and alkylation has been described to provide hypo-allergenic forms of these allergenic proteins. Hypo-allergenicity can be shown by reduced IgE-binding in solid phase immunoassays, or by activation effector-cells like basophils. However, the allergens Ara h2 and Ara h6 do not include all allergens found in peanut, and immunotherapy, or immunovaccination, solely based on Ara h2 and Ara h6, thus without other peanut allergens, is likely not sufficient to (prophylactically) treat, or desensitise, peanut allergic individuals.

Reduction and alkylation cleaves disulphide bonds in proteins irreversibly. Ara h2 has 4 disulfide bonds and Ara h6 has 6 disulfide bonds. It was shown that reduction and alkylation leads to a major change in secondary structure of Ara h2 and Ara h6 resulting in loss of IgE-binding and activation of effector-cells. However, considering that Ara h2 and, to a lesser extent, Ara h6 only form part of the peanut allergy causing agents, Ara h2 and Ara h6 exclusively are likely not sufficient to treat peanut allergic individuals.

It is an object, amongst other objects, of the present invention to provide pharmaceutical compositions, or formulations, for the therapeutic or prophylactic treatment of peanut allergies. In other words, it is an object, amongst other objects, of the present invention to provide pharmaceutical compositions, or formulations, for desensitising patients for peanuts, or more specifically peanut allergens.

These objects, amongst other objects, are met by a pharmaceutical composition as defined in the appended claims.

Specifically, according to a first aspect, these objects, amongst other objects, are met by pharmaceutical compositions comprising a modified whole peanut extract and pharmaceutically acceptable diluents and/or excipients, wherein said modified whole peanut extract is a reduced and subsequently alkylated whole peanut extract.

Within the context of the present invention, an allergen is defined as an antigen capable of stimulating a hypersensitivity reaction in atopic mammals through immunoglobulin E (IgE) responses. Most mammals mount significant immunoglobulin E responses only as a defence against parasitic infections. However, some mammals may respond to many common environmental antigens. This hereditary predisposition is also designated atopy. In atopic mammals, non-parasitic antigens stimulate undesired IgE production, resulting in hypersensitivity or allergy Within the context of the present invention, a whole peanut extract denotes a peanut extract comprising substantially all seed kernel proteins found in peanut. In other words, a whole peanut extract according to the present invention is representative for the proteins found in peanut and thereby for the causative agents (allergens) of peanut allergy. A whole peanut extract according to the present invention thus comprises, besides Ara h2 and Ara h6, also other peanut allergens amongst which the major peanut allergen Ara h1.

According to the present invention, the present whole peanut extract is modified by reduction and alkylation, thus the disulfide bonds present in the proteins of the whole peanut extract are broken followed by alkylation resulting in an irreversible change in the secondary structure of the proteins comprising disulphide bonds and thereby a destruction of allergenic reaction causing IgE epitopes in these proteins.

Suitable agents to reduce disulphide bonds are known and can, for example, be 2-mercaptoethanol (β-ME), dithiothreitol (DTT), dithioerythritol, cysteine, homocystein, tributylphosphine, sulfite, tris(2-carboxyethyl)phosphine (TCEP), sodium(cyano)borohydride, lye, glutathione, E-mercapto ethylamine, thioglycollic acid, methyl sulfide or ethyl sulfide.

Suitable agents to alkylate reduced cysteine residues are known and can, for example, be N-ethylmalimide, cystamine, iodoacetamide, iodoacetic acid, alkylhalogenides, alkylsulfates, alkenes, or enzymes.

Subjecting a whole peanut extract comprising the major allergenic protein Ara h1 to reduction and methylation thereby reducing the allergenicity thereof is surprising considering that, in contrast to Ara h2 and Ara h6, Ara h1 does not comprise disulfide bonds, only a single Cys residue. Accordingly, reduction and alkylation of Ara h1 is not expected to result in secondary structure changes and an accompanying loss of IgE-binding and activation of effector-cells of the whole peanut extract. Despite this, especially considering that Ara h1 is a major peanut allergen, the present inventors have surprisingly found that reduction and alkylation has an effect on Ara h1 and thereby the allergenicity of the modified peanut extract.

According to a preferred embodiment of this first aspect of the invention, the present whole peanut extract is a defatted before subjecting the peanut extract to reduction and alkylation. Removing lipids and other fatty substances increases the protein content of the extract and thereby the relative number of immunogenic IgE epitopes and thereby the allergenicity of the extract.

According to yet another preferred embodiment of this first aspect of the invention, the present whole peanut extract comprises soluble peanut kernel proteins, more preferably at least Ara h1, Ara h2 and Ara h6. Soluble peanut kernel proteins represent the majority, if not all, of the allergen causing epitopes of the peanut proteins Ara h1, Ara h2 and Ara h6.

According to an especially preferred embodiment of this first aspect of the invention, the present whole peanut extract is obtainable by:

a) grinding peanuts for providing a peanut powder;

b) incubating said peanuts in acetone during 30 minutes using 5 grams peanut powder per 50 ml acetone for providing a defatted peanut powder;

c) drying said defatted peanut powder;

d) suspending said dried peanut powder in a buffer with a pH between 7 and 9; and e) isolating the resulting supernatant of step (d) thereby providing a whole peanut extract.

The above method provides a purified extract of soluble peanut allergenic proteins, i.e. an extract enriched for soluble peanut kernel proteins, which can be readily subjected to a subsequent reduction and alkylation.

According to another especially preferred embodiment of this first aspect of the invention, the present pharmaceutical compositions further comprise aluminum. Surprisingly, it was found that adding aluminum to the present composition further reduced the allergenicity of the present modified whole peanut extract.

Because of the significantly reduced IgE binding, or IgE epitopes, the present pharmaceutical compositions are especially suitable to be used in a therapeutic treatment for desentizing a peanut allergy in a patient, preferably, by immunotherapy or immunovaccination.

According to the present invention immunotherapy comprises administering to a mammal, preferably a human mammal, suffering from an allergy the present composition in a sufficient amount and during sufficient time to reduce, or eliminate, an allergic response of said mammal to said allergen.

A typical sufficient amount will be from about 0.1 ng/kg to 10 mg/kg, 10 ng/kg to about 100 μg/kg, or 0.1 μg/kg to 1 μg/kg of the present composition relative to the body weight of the individual to which it is administered. Often, a treatment will comprise starting with the administration of dosages at the lower end of these ranges and increasing the dosages as the treatment progresses.

For desensitization treatment, it is typically necessary for the patient to receive frequent administrations, e.g., initially every one, two or three days, gradually reducing to once every two or three weeks. Other suitable desensitization programs include subcutaneous injections once every 2-4 weeks the dosage of which injections may gradually increase over a period of 3-6 months, and then continuing every 2-4 weeks for a period of up to about 5 years. It is also possible, particular for sublingual administration, that daily administrations are given.

Desensitization protocols may also comprise a form of treatment conventionally known in various equivalent alternative forms as rapid desensitization, rapid allergen immunotherapy, rapid allergen vaccination, and rapid or rush immunotherapy. In broad terms, this procedure aims to advance an allergic patient to an immunizing or maintenance dose of extract (i.e., allergen) by administering a series of injections (or via another suitable carrier) of increasing doses of the allergen at frequent (e.g. hourly) intervals. If successful, the patient will exhibit an improved resistance to the allergen, possibly even presenting a total non-reactivity to any subsequent allergen exposure.

Various desensitization protocols are known in the art and may for instance comprise a method of treating a patient having an immediate hypersensitivity to an allergen using an accelerated rapid immunotherapy schedule in combination with a method of pre-treating such patient with prednisone and histamine antagonists prior to receiving the accelerated immunotherapy.

The present invention will be further detailed in the following examples of preferred embodiments of the present invention. In the examples, reference is made to figures wherein:

FIG. 1: shows an rp-HPLC pattern of individual peanut allergens and extract of Spanish cultivar. Panel A (individual peanut allergens): Peak at 7.3 ml: Ara h2; peak at 9-9.5 ml: Ara h6; peak at 11 ml: Ara h1. Panel B (extract of Spanish cultivar): blank (MQ water); Peak at 7.3 ml: Ara h2; peak at 9-9.5 ml: Ara h6; peak at 11 ml: Ara h1;

FIG. 2: shows an rp-HPLC pattern of individual peanut allergens before and after modification. Top panel: Ara h1, arrow indicate before (native) and after (RA) modification. Middle panel: Ara h2, arrow indicate before (native) and after (RA) modification. Bottom panel: Ara h6, arrow indicate before (native) and after (RA) modification.

EXAMPLES

Example 1

Collection of Samples and Preparing Extracts

Twelve peanuts sample were generously supplied by Dr Maleki (US Department of Agriculture, New Orleans, USA), comprising four different cultivars (Runner, Spanish, Valencia and Virginia). These cultivars are commonly consumed in the Western Europe and USA. Parts of the peanuts were roasted (140° C. for 15 minutes in a preheated circulated hot air oven).

The peanuts were grinded manually and defatted with acetone (5 g peanut was defatted with 50 mL of acetone for 30 minutes), and left to dry overnight at room temperature (RT). 1 g of defatted peanut powder was suspended with 10 mL of 50 mM Tris HCl pH 8.0 (10% w/v) and stirred for 1 hour at RT. Subsequently the samples were centrifuged and the supernatants were filtrated trough 0.2 μm cellulose membrane filters (Whatman FP30/0.2 CA-S, Whatman GmbH, Dassel, Germany) and used for further studies.

The extracts were stored at −20° C. in aliquots for single use. Protein concentration was determined using the Bradford analysis. The standard curve was prepared with bovine serum albumin (BSA 2 mg/mL from Pierce, Ill., USA) and was diluted to a range of 50-500 μg/mL. Crude peanut extracts (CPEs) were diluted 40× with 50 mM Tris HCl pH 8.0. Protein assay reagent, from Bio-Rad, USA, was diluted 5× with water. Twenty μL of standards and samples were mixed with 1 mL of 5× diluted reagent and 250 μL of each samples and standards were put in the wells of a flat bottom plate with flat (F-type). 50 mM Tris HCl pH 8.0 was used as blank. Results are summarised in Table 1.

TABLE 1

Peanut samples and protein concentrations in their extracts.

| Cultivar | Name | Raw/Rosted | Protein (mg/mL) | Protein (mg/mL) | Mean (mg/mL) | RSD (%) | Extractability after roasting (%) |
|---|---|---|---|---|---|---|---|
| Runner | GA06G | Raw | 17.1 | 17.8 | 17.5 | 3.1 | |
| | Tiftguard | Raw | 19.7 | 18.2 | 19.0 | 5.3 | |
| | Florunner 4/14 | Raw | 14 | 13.2 | 13.6 | 4.0 | |
| | Florunner 4/14 | Roasted | 10.1 | 9.2 | 9.6 | 6.8 | 70.6 |
| Spanish | Olin Spanish | Raw | 23.0* | 19.5 | 21.2 | 11.9 | |
| | Olin Spanish | Roasted | 15.9 | 16.8 | 16.4 | 4.3 | 77.4 |
| Valencia | Valencia A | Raw | 15.9 | 13.5 | 14.7 | 11.4 | |
| | Valencia A | Roasted | 12.0 | 10.6 | 11.3 | 8.6 | 76.9 |
| Virginia | NC-v11 Virginia | Raw | 13.9 | 15.1 | 14.5 | 6.0 | |
| | NC-v11 Virginia | Roasted | 7.0 | 6.6 | 6.8 | 3.6 | 46.9 |
| | Gregory Virginia | Raw | 14.6 | 13.2 | 13.9 | 6.9 | |
| | Brantley Virginia | Raw | 16.1 | 14.5 | 15.3 | 7.3 | |

Example 2

Abundance of Ara h1, Ara h2, and Ara h6 in the Peanut Kernel

An rp-HPLC method was developed to quantify Ara h1, Ara h2, and Ara h6 using an Agilent 1200 series HPLC with a X-Bridge BEH Phenyl 3.5 μm column (2.1×150 mm, Waters, Ireland). Gradient elution was performed by using the following mobile phases: (A) 0.1% TFA in Mili Q (MQ) Water and (B) 0.085% TFA in Methanol. The gradient used was 3% eluent B/min, starting with 50% of eluent B until 100% for 15 minutes. Chromatograms were recorded at 280 nm and 215 nm. Recordings at 215 nm were used for comparing peak areas.

Samples were diluted to a protein concentration of 1 mg/mL with MQ water, and blank was MQ Water. Purified preparations of peanut allergens Ara h 1, Arah 2 and Ara h 6 were used to assign peaks. Separated peaks of major peanut allergens (Ara h 1, Ara h 2, and Ara h 6) were quantified and expressed as percentage of total protein area.

Figures 1, 1A:
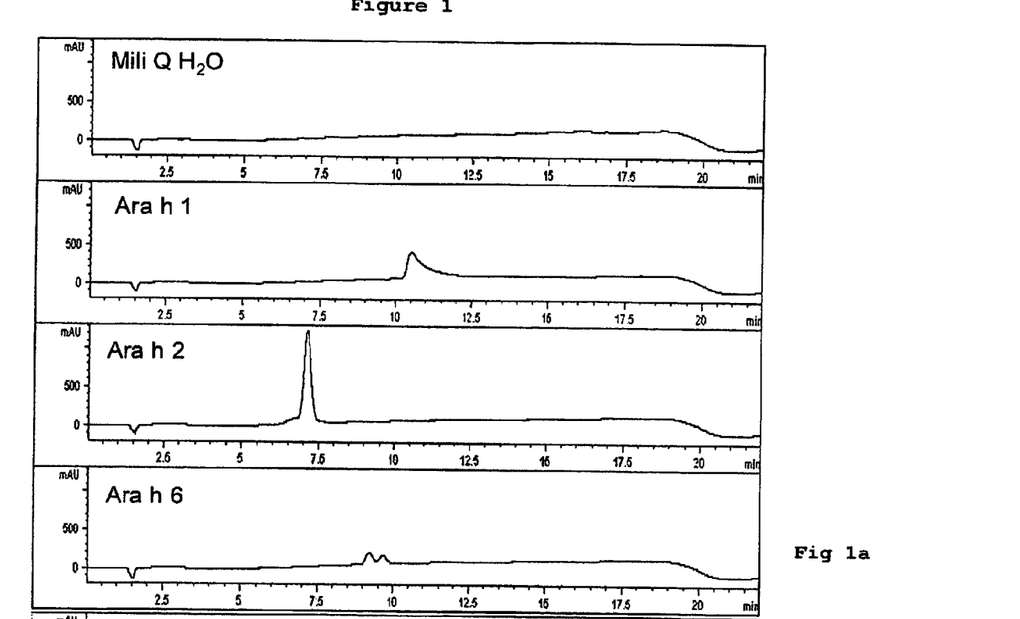

FIG. 1*a* shows an example of this analysis using the individual, purified forms of Ara h1, Ara h2, and Ara h6. These allergens are baseline separated and the method allows for quantification in extracts.

Figure 1B:
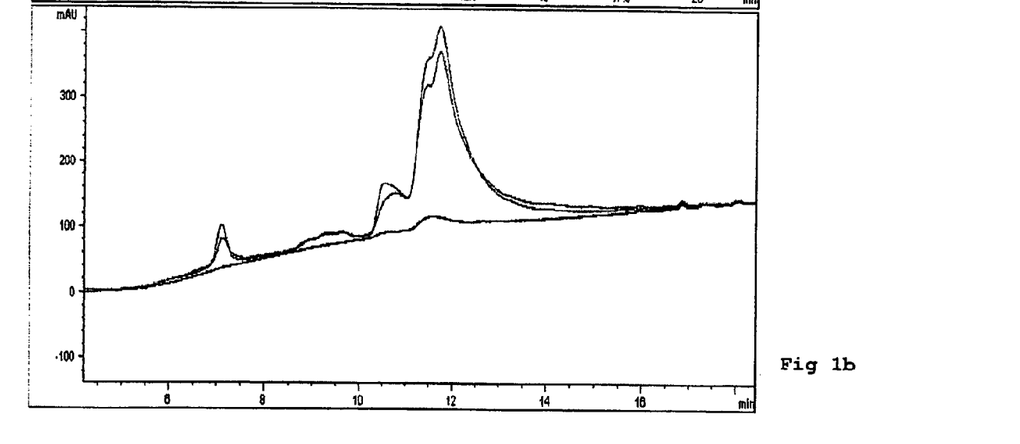

FIG. 1*b* shows an example of a peanut extracts and the arrows indicate the peaks corresponding to Ara h1, Ara h2, and Ara h6. It can be seen that Ara h1 is the more abundant allergen in this extracts.

All peanut samples were analysed for their Ara h1, Ara h2, and Ara h6 content as summarized in Table 2. For all tested samples, the content of Ara h1 is higher than that of Ara h2 and Ara h6.

TABLE 2

Content of Ara h1, Ara h2, and Ara h6 in peanut extracts.

| Cultivar | Name | Protein | | Retention time (min) | Area (%) | Area (mAU*s) |
|---|---|---|---|---|---|---|
| Runner | GA06G | Raw | Ara h 2 | 7.908 | 10 | 3518.8 |
| | | | Ara h 6 | 9.941 | 6 | 2069.6 |
| | | | Ara h 1 | 11.412 | 21 | 7393.2 |
| | Tiftguard | Raw | Ara h 2 | 7.925 | 12 | 6131.6 |
| | | | Ara h 6 | 9.961 | 4 | 2247.8 |
| | | | Ara h 1 | 11.412 | 16 | 8086.1 |
| | Florunner 4/14 | Raw | Ara h 2 | 7.087 | 12 | 3249.2 |
| | | | Ara h 6 | 9.672 | 6 | 1524.4 |
| | | | Ara h 1 | 10.6 | 24 | 6543.7 |
| | Florunner 4/14 | Roasted | Ara h 2 | 7.108 | 7 | 1857.7 |
| | | | Ara h 6 | 9.751 | 6 | 1435.5 |
| | | | Ara h 1 | 10.663 | 18 | 4594.6 |
| Spanish* | Olin Spanish | Raw | Ara h 2 | 7.086 | 7 | 998.2 |
| | | | Ara h 6 | 9.621 | 6 | 850.9 |
| | | | Ara h 1 | 10.491 | 11 | 1615.9 |
| | Olin Spanish | Roasted | Ara h 2 | 7.11 | 4 | 705.9 |
| | | | Ara h 6 | 9.65 | 5 | 875.4 |
| | | | Ara h 1 | 10.557 | 6 | 989.1 |
| Valencia | Valencia A | Raw | Ara h 2 | 7.879 | 10 | 4403.7 |
| | | | Ara h 6 | 9.917 | 8 | 3503 |
| | | | Ara h 1 | 11.37 | 17 | 7174.9 |
| | Valencia A | Roasted | Ara h 2 | 7.907 | 5 | 2147.1 |
| | | | Ara h 6 | 9.945 | 4 | 1681.5 |
| | | | Ara h 1 | 11.378 | 7 | 2916.8 |
| Virginia | NC-v11 Virginia | Roasted | Ara h 2 | 7.311 | 8 | 1493.9 |
| | | | Ara h 6 | 9.957 | 11 | 1966 |
| | | | Ara h 1 | 10.941 | 5 | 994.6 |
| | NC-v11 Virginia | Raw | Ara h 2 | 7.246 | 8 | 2141 |
| | | | Ara h 6 | 9.85 | 5 | 1306.2 |
| | | | Ara h 1 | 10.856 | 13 | 3371.2 |
| | Gregory Virginia | Raw | Ara h 2 | 7.815 | 16 | 4441.4 |
| | | | Ara h 6 | 9.865 | 14 | 3894.4 |
| | | | Ara h 1 | 11.288 | 32 | 8697.7 |
| | Brantley Virginia | Raw | Ara h 2 | 7.807 | 12 | 3543.4 |
| | | | Ara h 6 | 9.862 | 12 | 3517.3 |
| | | | Ara h 1 | 11.341 | 17 | 5121.2 |

In all tested samples, Ara h1 is more abundant than Ara h2 or Ara h6.

Example 3

Modification Affects Ara h2 and Ara h6, but not Ara h1

Figure 2:
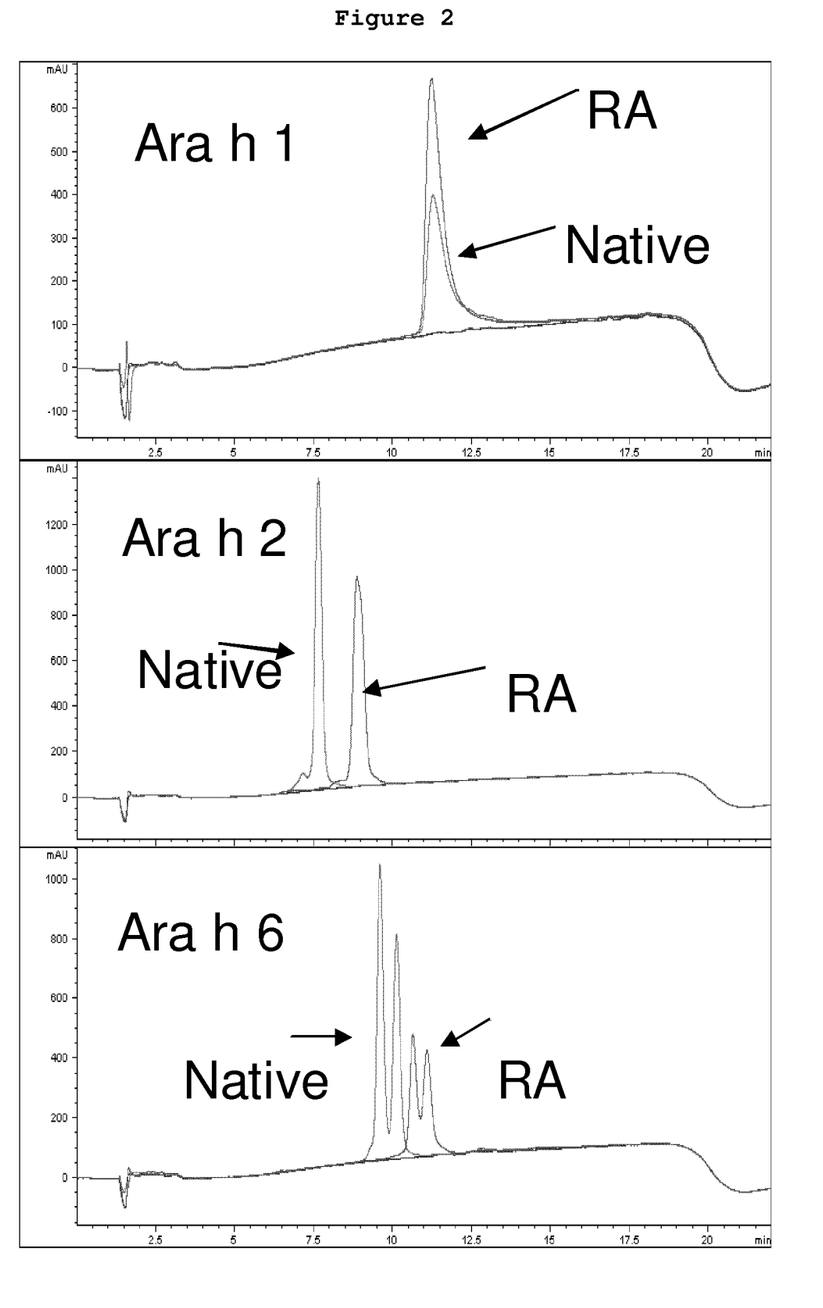
Figure 3:
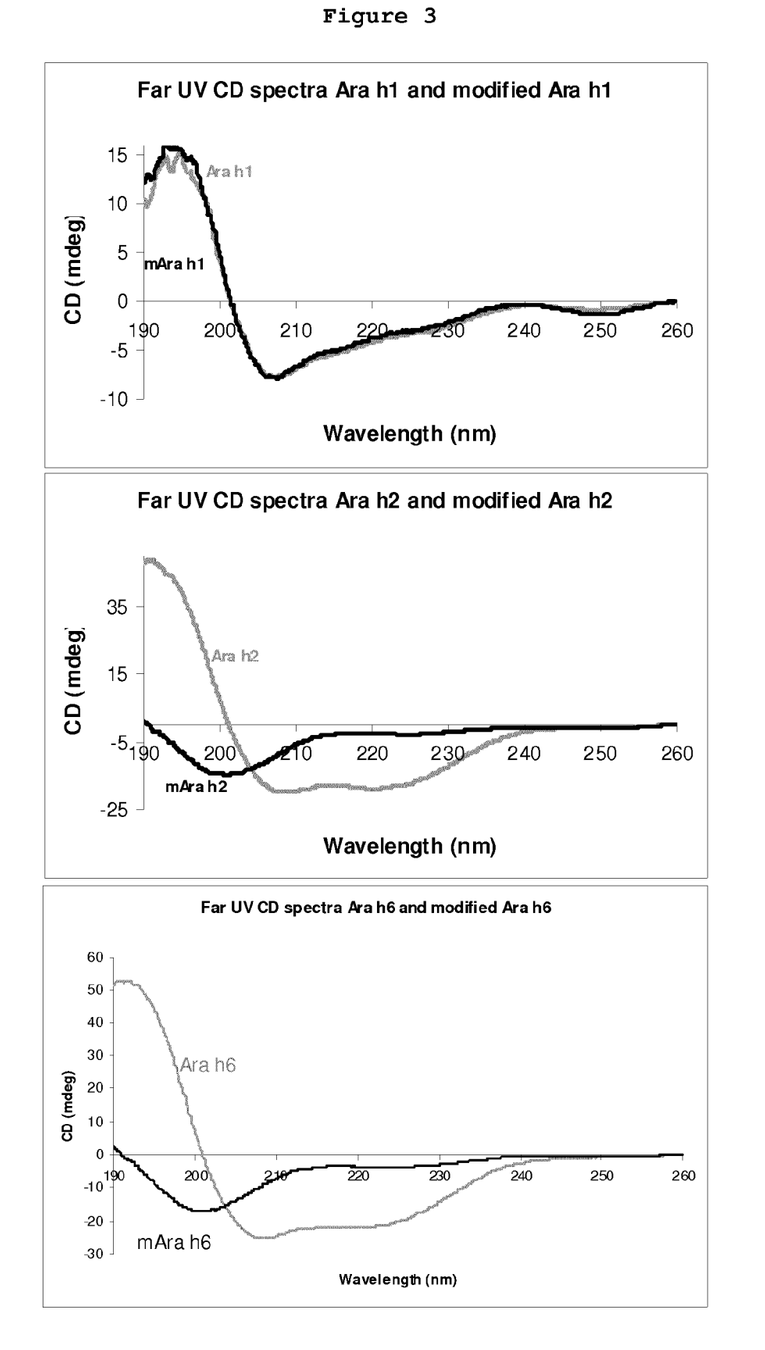
FIG. 3: shows far UV CD spectra of individual peanut allergens before and after modification. Top panel: Ara h1, arrow indicate before (native) and after (RA) modification. Middle panel: Ara h2, arrow indicate before (native) and after (RA) modification. Bottom panel: Ara h6, arrow indicate before (native) and after (RA) modification.

Purified allergens Ara h1, Ara h2, and Ara h6 were treated as described earlier. In short, the allergens were incubated with DTT for one hour at 60° C. and IAA was added and the mixture was incubated ar room temperature for 1.5 hours. Treated allergens were tested by rp-HPLC to establish if their mobility was affected. In FIG. 2, it can be clearly seen that Ara h1 is not affected by this modification, while Ara h2 and Ara h6 are. To further investigate this, another test was applied: far UV CD spectroscopy by which the content of secondary structure elements in purified proteins can be estimated. Spectra were normalized for protein concentration. FIG. 3 shows that the modification affects Ara h2 and Ara h6, while Ara h1 is not affected.

Example 4

Reduced and Alkylated Peanut Extract has Low IgE-Binding Potency

Serum from 20 patients with a peanut allergy was obtained and IgE ELISA. ELISA plates were coated with peanut extract and IgE-binding potency of native peanut extract was defined as 1, and the IgE-binding potency of modified peanut extract was related thereto. Table 3 shows per patient the rest potency of modified peanut extract relative to native peanut extract. The mean rest potency of modified peanut extract is 7% of the potency of native peanut extract.

TABLE 3

Potency of modified peanut extract relative to native extract for individual patients.

| Serum number | Rest potency of modified peanut extract |
|---|---|
| D19 | 0.013 |
| D44 | 0.004 |
| D48 | 0.169 |
| D50 | 0.014 |
| D60 | 0.053 |
| D62 | 0.041 |
| D64 | 0.178 |
| D65 | 0.003 |
| D68 | 0.043 |
| D69 | 0.113 |
| D70 | 0.091 |
| D74 | 0.045 |
| D77 | 0.118 |
| D80 | 0.028 |
| D81 | 0.082 |
| D98 | 0.082 |
| D103 | 0.122 |
| D105 | 0.062 |
| D107 | 0.088 |
| D114 | 0.059 |
| Mean | 0.072 ± 0.05 |

Example 5

In Vivo Safety of Modified Peanut Extract

Figure 4:
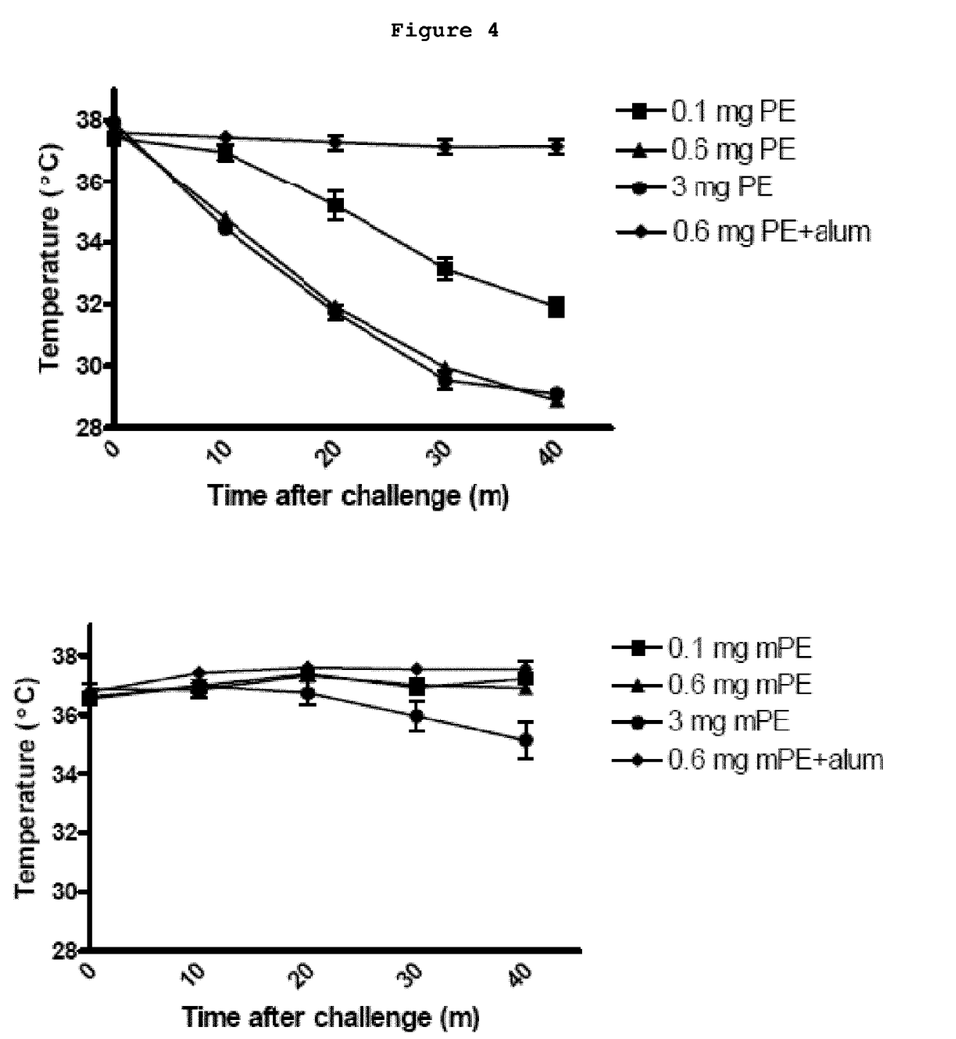
FIG. 4: shows body temperature of peanut-allergic mice after challenge. Top panel: Challenge with native peanut extract (0.1, 0.6, and 3 mg/mouse). Bottom panel: Challenge with modified peanut extract (0.1, 0.6, and 3 mg/mouse)

Mice were made allergic to peanut extract as described earlier. These mice (6 per group) were challenged either with native or modified peanut extract. Body temperature was followed for 90 minutes. The temperature plots are shown in FIG. 4.

It can be clearly seen that a challenge with native peanut extract result in a severe allergic reaction with a quick and deep drop in body temperature. This occurs already at a dose of 0.1 mg/ml. In contrast, challenge with modified peanut extract did not result in such reaction, not even at a 30-fold higher dose (3 mg/mouse).

Examples 6 and 7

Introduction

In in vivo mouse models for peanut allergy immunotherapy, test preparations were analyzed for efficacy. These examples demonstrate the potential of a chemically modified peanut extract (with or without adsorption to aluminum hydroxide) to be effectively used to treat mice that have been sensitized to peanut.

Material and Methods

Mice

Five-week-old specific pathogen-free female C3H/HeOuJ mice were purchased from Charles River, France. All mice were housed under specific pathogen-free conditions within the animal care facility at the Utrecht University, The Netherlands. Experiments were approved by the Animal Experiments Committee of the Utrecht University. The diet used contained vegetable protein (including soy) but was free of peanut proteins.

Sensitization and Challenge

Figure 5:
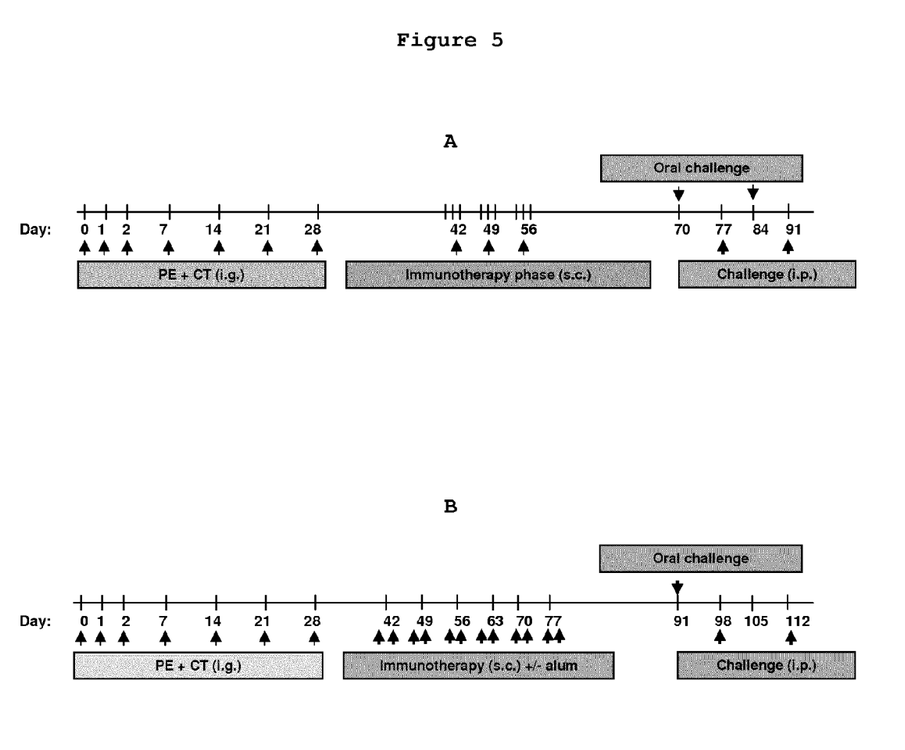
FIG. 5: shows the time line of the sensitization, de-sensitization and challenge protocol used in example 6(A) and the time line of the sensitization, de-sensitization and challenge protocol used in example 7(B)

Mice (n=6 per group) were sensitized by intragastric (i.g.) administration of 6 mg peanut extract (PE) and 15 µg Cholera Toxin (CT, List Biological Laboratories, Inc.) in 400 µl PBS per mouse on days 0, 1, 2, 7, 14, 21, 28. Control mice received PBS with 15 µg CT/mouse in 400 µl PBS per mouse. From day 42, different groups of mice were subcutaneously (s.c.) de-sensitized in the neck, three times a week for three weeks (example 5) or twice a week for six weeks (example 6), with 200 µl of the different test preparations (modified PE+/−aluminum hydroxide) or their respective control (FIG. 5). Below, groups of non-allergic PBS sensitized mice and allergic PE sensitized mice (without immunotherapy) are depicted as PBS control and PE control, respectively.

Assessment of Anaphylaxis

As an objective parameter of anaphylactic shock, body temperature was measured by means of rectal thermometry every 10-20 minutes for 90 minutes after i.p. challenge. At several time points during the course of the model, blood was taken for the measurement of antibodies and mMCP-1 (mast cell protease 1). On day 91 (example 5) or 112 (example 6), directly after mice were challenged i.p., their body temperature was followed for 90 minutes.

Example 6

Results

Figure 6:
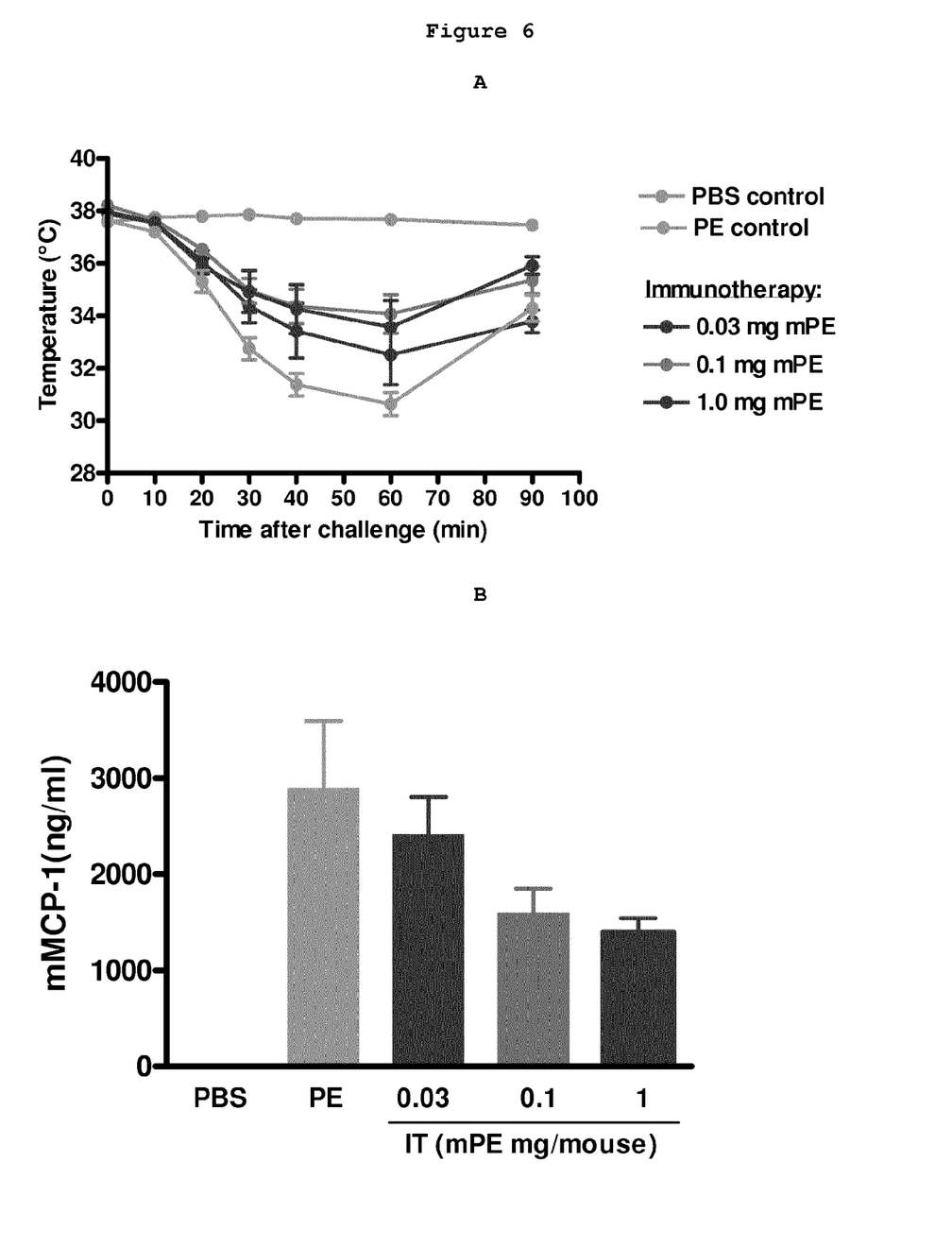
FIG. 6: shows the temperature (A) of mice challenged on day 91 and mast cell activation (B; mMCP-1) on day 85.

After i.p. challenge on day 91, the modified PE preparation effectively reduced the anaphylactic response as measured by the drop in temperature after challenge (FIG. 6A). De-sensitization with different concentrations modified PE, demonstrated a small dose-dependent effect comparing 0.03 and 0.1 mg on the improvement of the anaphylactic shock response as measured by temperature (FIG. 6A).

No difference in temperature is observed comparing the 2 highest concentrations 0.1 and 1 mg mPE (FIG. 6A). The improvement of the anaphylactic shock response as demonstrated by the smaller drop in temperature after immunotherapy with mPE, is similarly demonstrated by the levels of mast cell activation (mMCP-1; FIG. 6B) on day 85. The lowest dose tested (0.03 mg/mouse) did not results in an improvement while the 2 higher IT dosages (0.1 and 1 mg/mouse respectively) demonstrated a decreased activation of mast cells.

Example 7

Results

Figure 7:
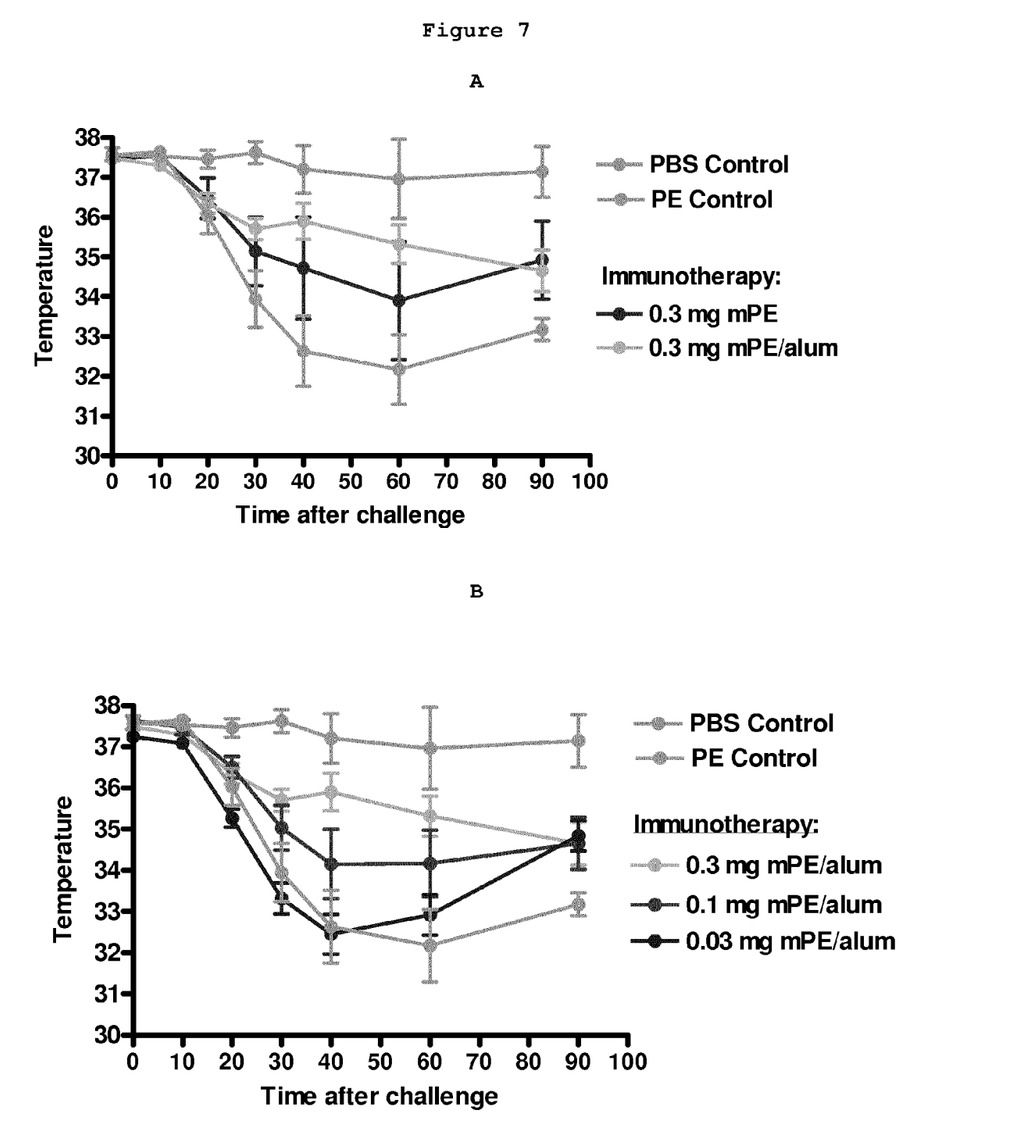
FIG. 7: shows the temperature of mice challenged on day 112.

After i.p. challenge on day 112, both immunotherapy preparations (modified PE alone and adsorbed to alum) effectively reduced the anaphylactic response as measured by the drop in temperature after challenge (FIG. 7).

The alum-adsorbed extract showed a slightly improved efficacy profile compared to the non-adsorbed extract (FIG. 7A). De-sensitization with different concentrations modified PE adsorbed to alum, demonstrated a dose-dependent effect on the improvement of the anaphylactic shock response as measure by temperature (FIG. 7).

Figure 8:
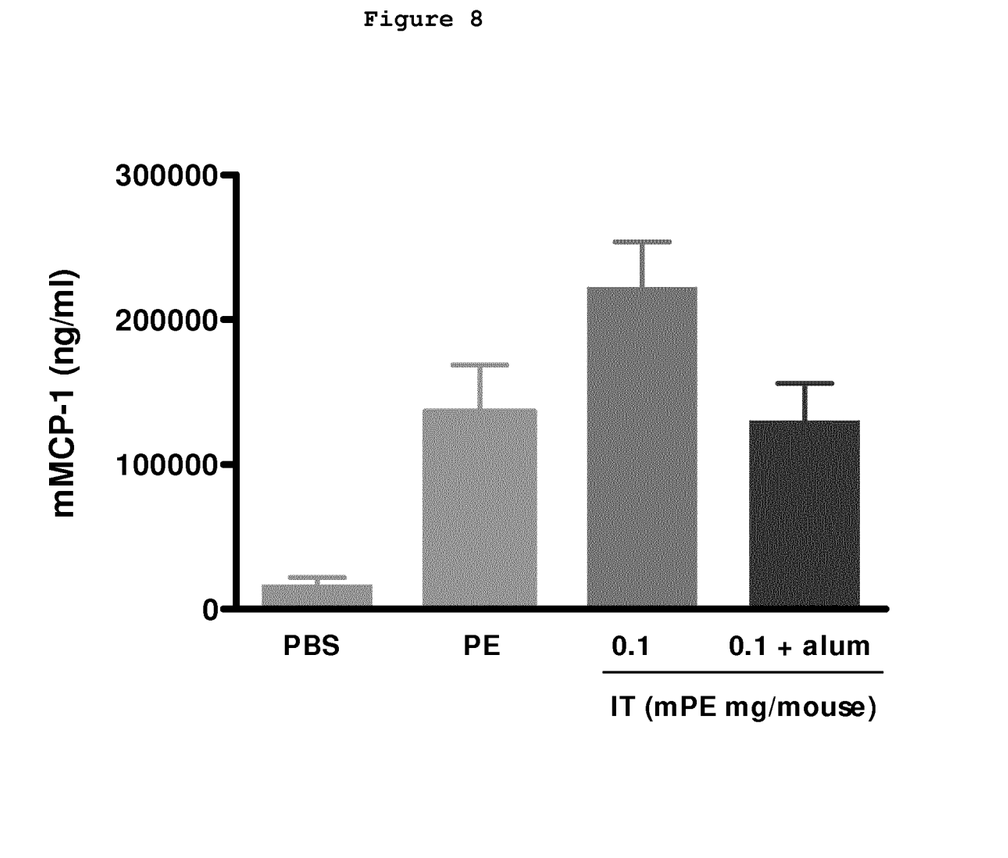
FIG. 8: shows the level of mMCP-1 in serum of all groups tested on day 99.
Figure 9:
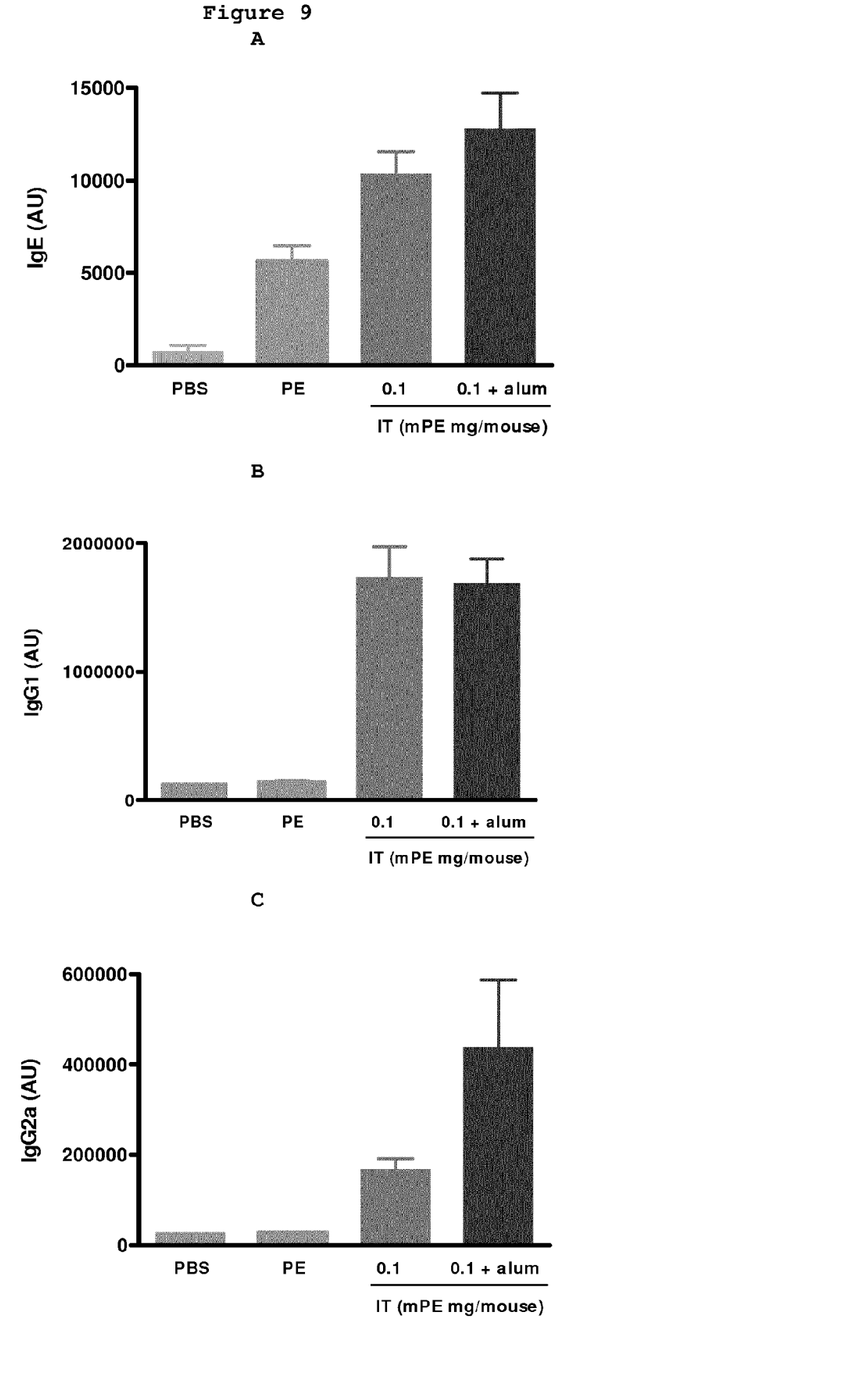
FIG. 9: shows levels of IgE (A), IgG1 (B) and IgG2a (C) in serum of all groups tested on day 99.

Levels of mMCP-1 and antibodies (IgE, IgG1 and IgG2a) were determined in the serum of all groups during the course of the model. The effect of immunotherapy on these immunological parameters on day 99 are shown (FIGS. 8 and 9).

MMCP-1 levels were elevated in all groups compared to the negative PBS control. The group de-sensitized with modified PE showed an increase in mMCP-1 compared to the mice that did not receive immunotherapy (PE control) and the mice that was de-sensitized with alum-adsorbed modified PE (FIG. 8).

IgE levels were greater in all groups compared to the negative PBS control. As commonly seen in the clinic, immunotherapy causes an increase in the level of IgE (FIG. 9A). This demonstrates the boost of the immune system due to immunotherapy. The elevation is greater during the course of the injections and slightly decreases in time (data not shown).

Mice that received immunotherapy displayed an increased level of IgG1 in the serum with comparable levels between the alum-adsorbed and non-adsorbed extract (FIG. 9B). The increase of IgG2a levels (comparable with IgG4 in human) is dominated by the group treated with the alum-adsorbed peanut preparation (FIG. 9C).

Conclusion

A peanut extract modified by reduction and alkylation is capable of improving the anaphylactic response in mice after i.p. challenge. Different immunotherapy models (s.c. injections three times a week for 3 weeks or twice a week for 6 weeks) demonstrated comparable efficacious results. Efficacy is slightly greater after the adsorption of the peanut extract to aluminum hydroxide. This could be due to the elevated levels of IgG2a (comparable to IgG4 in human) in the serum of these mice.

The invention claimed is:

1. A pharmaceutical composition comprising a modified whole peanut extract and pharmaceutically acceptable diluents and/or excipients, wherein said modified whole peanut extract is a reduced and subsequently alkylated whole peanut extract and is adsorbed to aluminium hydroxide.

2. The pharmaceutical composition according to claim 1, wherein said whole peanut extract is defatted.

3. The pharmaceutical composition according to claim 1, wherein said whole peanut extract comprises soluble peanut kernel proteins.

4. The pharmaceutical composition according to claim 1 wherein said whole peanut extract comprises Ara h1, Ara h2 and Ara h6.

5. The pharmaceutical composition according to claim 1, wherein said whole peanut extract is obtainable by:
   a) grinding peanuts for providing a peanut powder;
   b) incubating said peanuts in acetone during 30 minutes using 5 grams peanut powder per 50 ml acetone for providing a defatted peanut powder;
   c) drying said defatted peanut powder;
   d) suspending said dried peanut powder in a buffer with a pH between 7 and 9; and
   e) isolating the resulting supernatant of step (d) thereby providing a whole peanut extract.

6. The pharmaceutical composition according to claim 1 for use in immunotherapy to treat a mammal suffering from an allergy.

7. The pharmaceutical composition according to claim 6, wherein said mammal is a human mammal.

8. The pharmaceutical composition according to claim 1 for use in a therapeutic treatment for desensitizing the immune system of a mammal for said allergen or the use in a prophylactic treatment of a mammal with high predisposition for developing an allergy upon contact with said allergen.

9. The pharmaceutical composition according to claim 8, wherein said mammal is a human mammal.

10. The pharmaceutical composition according to claim 1 for use in medicine.

11. A method for immunotherapy, the method comprising administering to a mammal suffering from an allergy, or a mammal at risk of developing an allergy, a composition according to claim 1 in a sufficient amount and during sufficient time to reduce, or eliminate, an allergic response of said mammal to said allergen.

12. A method according to claim 11, wherein said mammal is a human mammal.

13. The method of claim 11, wherein the composition is administered in a sufficient amount and during sufficient time to increase an IgG response of said mammal to said allergen compared to an IgG response to said allergen of a mammal to which the composition is not administered.

* * * * *